US012741109B2

(12) United States Patent
Wang et al.

(10) Patent No.: US 12,741,109 B2
(45) Date of Patent: Sep. 22, 2026

(54) AUTOMATIC DOSAGE-CONTROLLED ATOMIZER, AND RESPIRATION SENSOR

(71) Applicant: National Tsing Hua University, Hsinchu City (TW)

(72) Inventors: Ting-Wei Wang, Hsinchu City (TW); Shih-Hua Ni, Tainan City (TW)

(73) Assignee: NATIONAL TSING HUA UNIVERSITY, Hsinchu City (TW)

( * ) Notice: Subject to any disclaimer, the term of this patent is extended or adjusted under 35 U.S.C. 154(b) by 471 days.

(21) Appl. No.: 18/406,792

(22) Filed: Jan. 8, 2024

(65) Prior Publication Data

US 2025/0041543 A1 Feb. 6, 2025

(30) Foreign Application Priority Data

Jul. 31, 2023 (TW) ................................ 112128569

(51) Int. Cl.
*A61M 15/00* (2006.01)
*A61M 11/00* (2006.01)

(52) U.S. Cl.
CPC ........ *A61M 15/0085* (2013.01); *A61M 11/00* (2013.01); *A61M 15/0065* (2013.01); *A61M 2205/3317* (2013.01); *A61M 2205/50* (2013.01); *A61M 2205/52* (2013.01); *A61M 2230/42* (2013.01)

(58) Field of Classification Search
CPC .... A61M 11/00; A61M 11/005; A61M 15/00; A61M 15/0065; A61M 15/0081; A61M 15/0085; A61M 2205/3317; A61M 2205/52; A61M 2230/42; A24F 40/50; A24F 40/51
See application file for complete search history.

(56) References Cited

U.S. PATENT DOCUMENTS

2024/0172791 A1* 5/2024 Ajpli ....................... A24F 40/10

FOREIGN PATENT DOCUMENTS

CN 104736053 A 6/2015
CN 106353373 A 1/2017
(Continued)

OTHER PUBLICATIONS

Machine translation of CN-114588425-A.*
Machine translation of CN-116088380-A.*

*Primary Examiner* — Joseph D. Boecker
(74) *Attorney, Agent, or Firm* — Birch, Stewart, Kolasch & Birch, LLP

(57) ABSTRACT

An automatic dosage-controlled atomizer includes a medication atomizer and a respiration sensor. The respiration sensor includes a capacitive electrode assembly that has a varying capacitance correlated to a respiratory airflow from a user, a resonant circuit that generates a resonant signal based on the varying capacitance, a signal analyzing circuit that obtains a detected vital capacity value and a period time data piece related to a breathing cycle of the user based on a frequency variation of the resonant signal, and an atomization adjustment module that generates a cumulative effective inhaled dose value based on the detected vital capacity value and the period time data piece. The atomization adjustment module causes the medication atomizer to stop generation of an aerosol airflow when the cumulative effective inhaled dose value exceeds a predetermined dose threshold value.

10 Claims, 9 Drawing Sheets

(56) References Cited

FOREIGN PATENT DOCUMENTS

| | | | | | |
|---|---|---|---|---|---|
| CN | 114588425 A | * | 6/2022 | .......... | A61M 11/005 |
| CN | 116088380 A | * | 5/2023 | ............ | A61M 11/00 |
| TW | 201617102 A | | 5/2016 | | |
| TW | 201944911 A | | 12/2019 | | |

* cited by examiner

AUTOMATIC DOSAGE-CONTROLLED ATOMIZER, AND RESPIRATION SENSOR

CROSS-REFERENCE TO RELATED APPLICATION

This application claims priority to Taiwanese Invention Patent Application No. 112128569, filed on Jul. 31, 2023, and incorporated by reference herein in its entirety.

FIELD

The disclosure relates to an atomizer that performs medication atomization and real-time respiration monitoring, and more particularly to an automatic dosage-controlled atomizer and a respiration sensor.

BACKGROUND

Inhalation therapy is a medication delivery technique that transports medication into a human respiratory system, allowing the medication to quickly reach the lungs and take effect. Therefore, it is widely employed in treatment of respiratory symptoms. Inhalers play a vital role in inhalation therapy, and their atomization performance parameters include, for example, atomized particle size, atomization rate, etc., which may affect efficacy of the medication.

Inhalers may be categorized into several types, such as dry powder inhalers, metered-dose inhalers, soft mist inhalers, nebulizers, etc., based on different drug characteristics and product technologies. However, improper usage may lead to suboptimal inhalation outcomes and even impact correctness in assessment of a patient's condition. According to statistics, over eighty percent of patients have experienced errors when using inhalers, making it challenging to ascertain the actual amount of inhaled medication.

SUMMARY

Therefore, an object of the disclosure is to provide an automatic dosage-controlled atomizer that can provide precise medication.

According to the disclosure, the automatic dosage-controlled atomizer includes a medication atomizer and a respiration sensor. The medication atomizer is configured to generate an aerosol airflow, and includes a nozzle for delivering the aerosol airflow. The respiration sensor includes a capacitive electrode assembly, a resonant circuit, a signal analyzing circuit and an atomization adjustment module. The capacitive electrode assembly is mounted to the nozzle, is disposed to receive a respiratory airflow from a user who is using the automatic dosage-controlled atomizer, and is configured to have a varying capacitance which is positively correlated to a flow rate of the respiratory airflow. The resonant circuit is configured to have a reference inductance and a reference capacitance, and is connected to the capacitive electrode assembly in parallel, so as to induce a total capacitance equaling a sum of the varying capacitance and the reference capacitance for a combined circuit of said capacitive electrode assembly and said resonant circuit. The signal analyzing circuit is electrically connected to the resonant circuit, and is configured to generate and send a feed signal to the resonant circuit in such a way that the resonant circuit generates a resonant signal based on the feed signal, and to perform frequency analysis on the resonant signal to generate a frequency variation signal indicating a frequency variation of the resonant signal. The frequency variation of the resonant signal is related to the varying capacitance. The atomization adjustment module is electrically connected to the signal analyzing circuit and the medication atomizer. The signal analyzing circuit includes a database that records a plurality of vital capacity values, and a plurality of reference frequency variation values that respectively correspond to the vital capacity values. The signal analyzing circuit is configured to, based on the database, determine one of the vital capacity values that corresponds to the frequency variation of the resonant signal to be a detected vital capacity value by comparing the frequency variation of the resonant signal with the reference frequency variation values. The signal analyzing circuit is configured to perform periodic analysis on the frequency variation signal to obtain a period time data piece related to the frequency variation signal. The period time data piece includes an inhalation time value and an exhalation time value. The atomization adjustment module is configured to receive the detected vital capacity value and the period time data piece from the signal analyzing circuit, and to generate a cumulative effective inhaled dose value based on the detected vital capacity value and the period time data piece. The atomization adjustment module is configured to compare the cumulative effective inhaled dose value with a predetermined dose threshold value to generate and send a control signal to the medication atomizer in such a way that the medication atomizer stops generation of the aerosol airflow when the cumulative effective inhaled dose value exceeds the predetermined dose threshold value.

Another object of the disclosure is to provide a respiration sensor for use with a medication atomizer.

According to the disclosure, the medication atomizer is configured to generate an aerosol airflow, and includes a nozzle for delivering the aerosol airflow. The respiration sensor includes a capacitive electrode assembly, a resonant circuit, a signal analyzing circuit and an atomization adjustment module. The capacitive electrode assembly is to be mounted to the nozzle, is disposed to receive a respiratory airflow from a user, and is configured to have a varying capacitance which is positively correlated to a flow rate of the respiratory airflow. The resonant circuit is configured to have a reference inductance and a reference capacitance, and is connected to the capacitive electrode assembly in parallel. The signal analyzing circuit is electrically connected to the resonant circuit, and is configured to generate and send a feed signal to the resonant circuit in such a way that the resonant circuit generates a resonant signal based on the feed signal, and to perform frequency analysis on the resonant signal to generate a frequency variation signal indicating a frequency variation of the resonant signal. The frequency variation of the resonant signal is related to the varying capacitance. The atomization adjustment module is electrically connected to the signal analyzing circuit and is to be connected to the medication atomizer. The signal analyzing circuit includes a database that records a plurality of vital capacity values, and a plurality of reference frequency variation values that respectively correspond to the vital capacity values. The signal analyzing circuit is configured to, based on the database, determine a detected vital capacity value that is one of the vital capacity values and that corresponds to the frequency variation of the resonant signal by comparing the frequency variation of the resonant signal with the reference frequency variation values. The signal analyzing circuit is configured to perform periodic analysis on the frequency variation signal to obtain a period time data piece related to the frequency variation signal. The period time data piece includes an inhalation time value and an exhalation time value. The atomization adjustment module is configured to receive the detected vital capacity value and the period time data piece from the signal analyzing circuit, and to generate a cumulative effective inhaled dose value based on the detected vital capacity value and the period time data piece. The atomization adjustment module is configured to compare the cumulative effective inhaled dose value with a predetermined dose threshold value to generate and send a control signal to the medication atomizer in such a way that the medication atomizer stops generation of the aerosol airflow when the cumulative effective inhaled dose value exceeds the predetermined dose threshold value.

BRIEF DESCRIPTION OF THE DRAWINGS

Other features and advantages of the disclosure will become apparent in the following detailed description of the embodiment(s) with reference to the accompanying drawings. It is noted that various features may not be drawn to scale.

DETAILED DESCRIPTION

Figure 1:
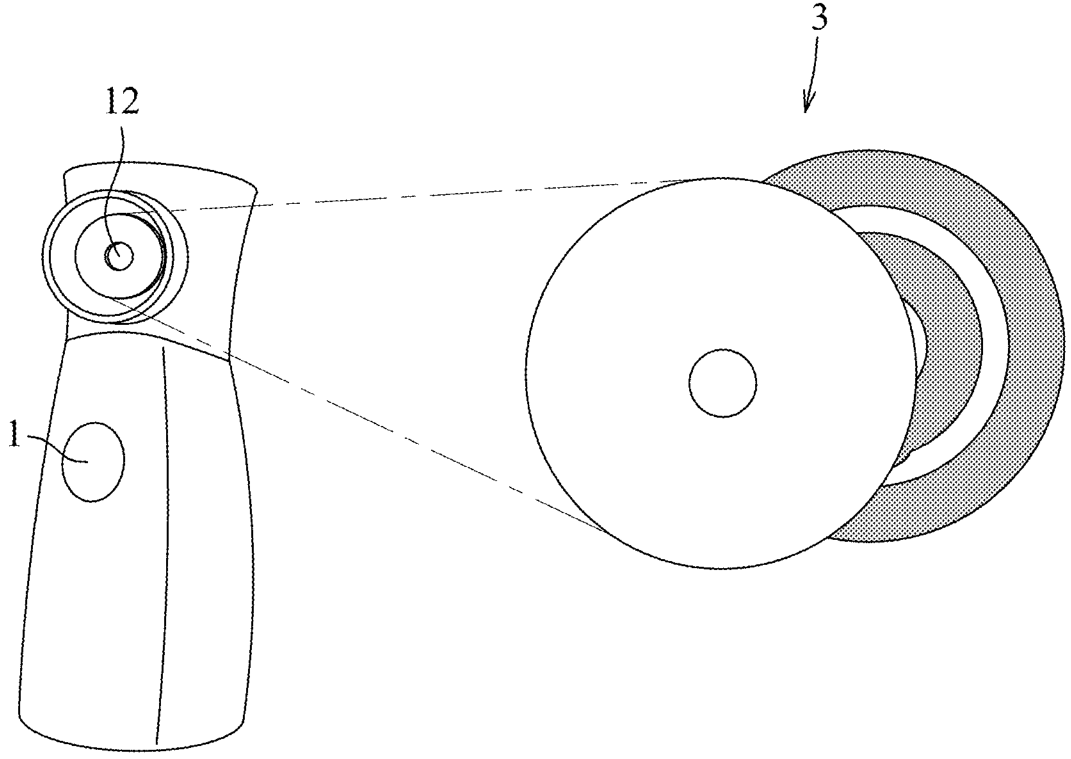
FIG. 1 is a perspective view illustrating an embodiment of an automatic dosage-controlled atomizer according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 2:
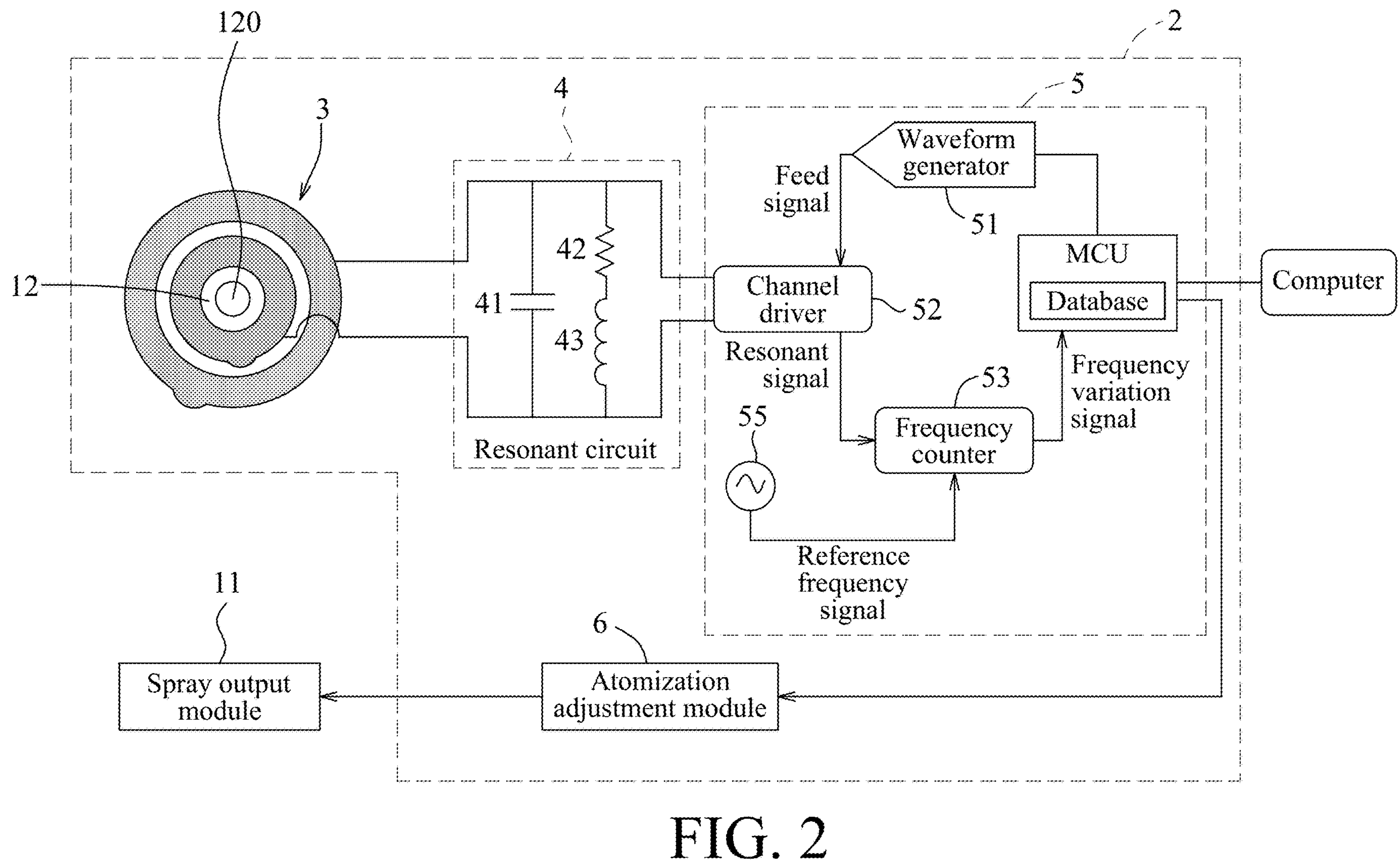
FIG. 2 is a block diagram illustrating a respiration sensor of the embodiment.

Referring to FIGS. 1 and 2, an embodiment of an automatic dosage-controlled atomizer according to this disclosure is shown to include a medication atomizer 1 and a respiration sensor 2.

The medication atomizer 1 includes a spray output module 11 configured to generate an aerosol airflow, and a nozzle 12 for delivering the aerosol airflow. In some embodiments, the spray output module 11 may include a container for accommodating medication, a compressor or an ultrasonic oscillator for atomizing the medication, and a motor or a fan for delivering the atomized medication, but this disclosure is not limited in this respect.

The respiration sensor 2 is attached to the medication atomizer 1, and includes a capacitive electrode assembly 3, a resonant circuit 4, a signal analyzing circuit 5 and an atomization adjustment module 6.

Figure 3:
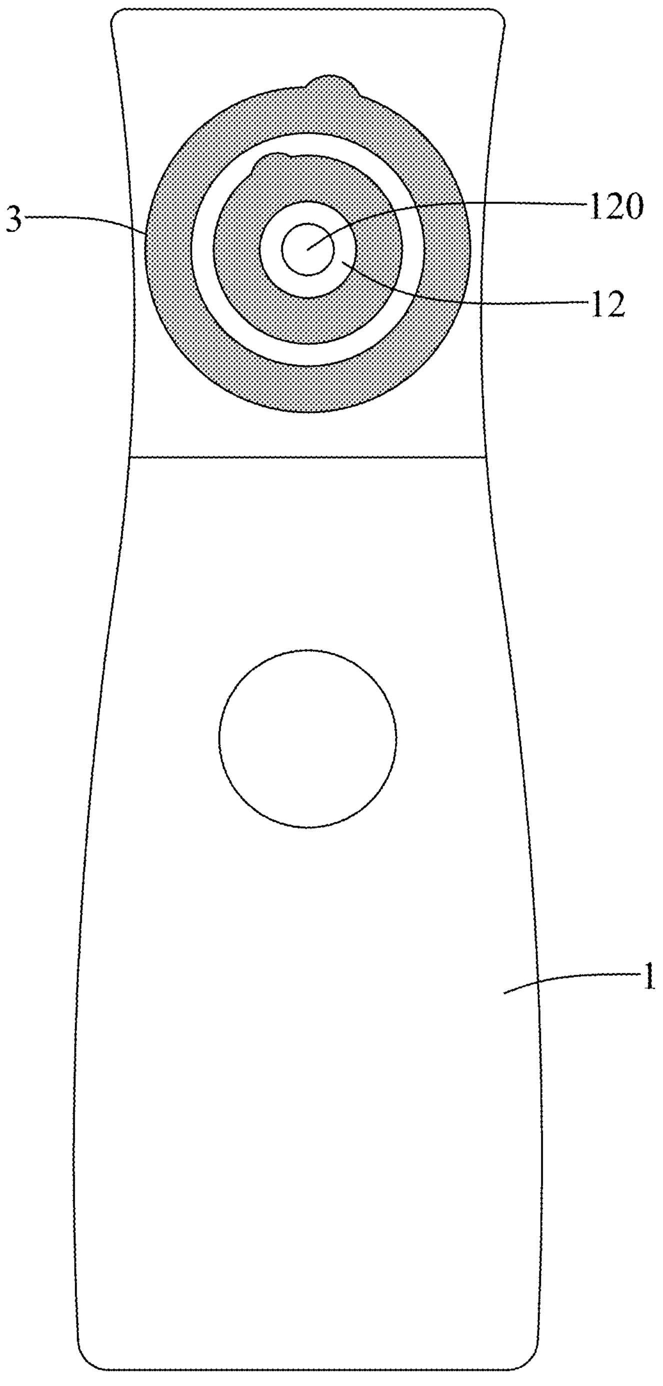
FIG. 3 is a schematic diagram illustrating a capacitive electrode assembly that is mounted to a nozzle of the embodiment.
Figure 4:
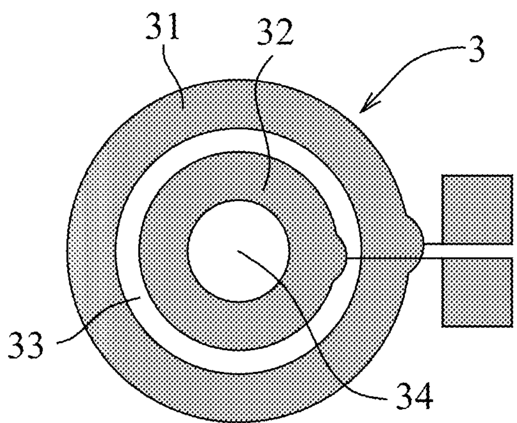
FIG. 4 is a schematic diagram illustrating a first exemplary layout of the capacitive electrode assembly.
Figure 5:
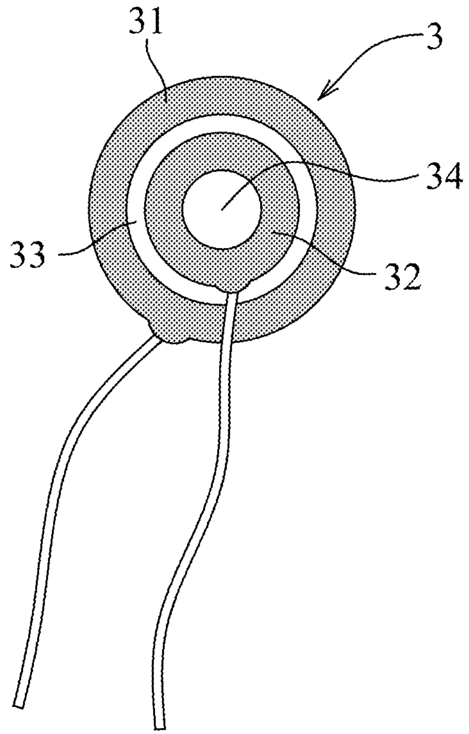
FIG. 5 is a schematic diagram illustrating an implementation of the capacitive electrode assembly.
Figure 7:
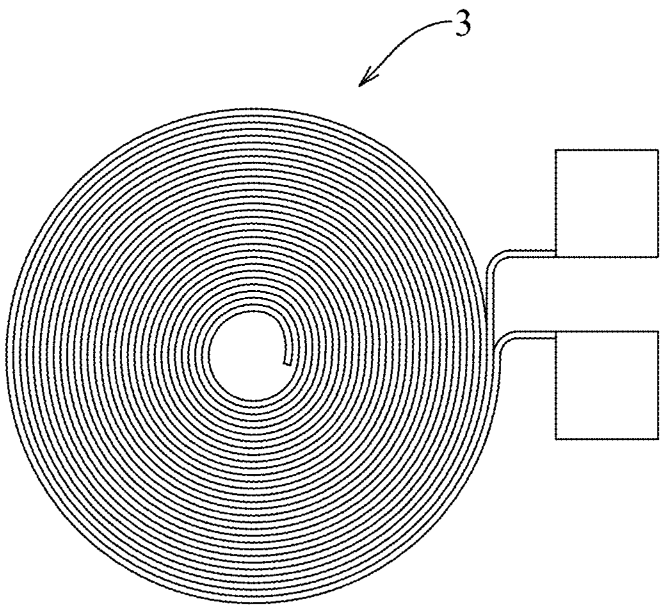
FIG. 7 is a schematic diagram illustrating a second exemplary layout of the capacitive electrode assembly.
Figure 8:
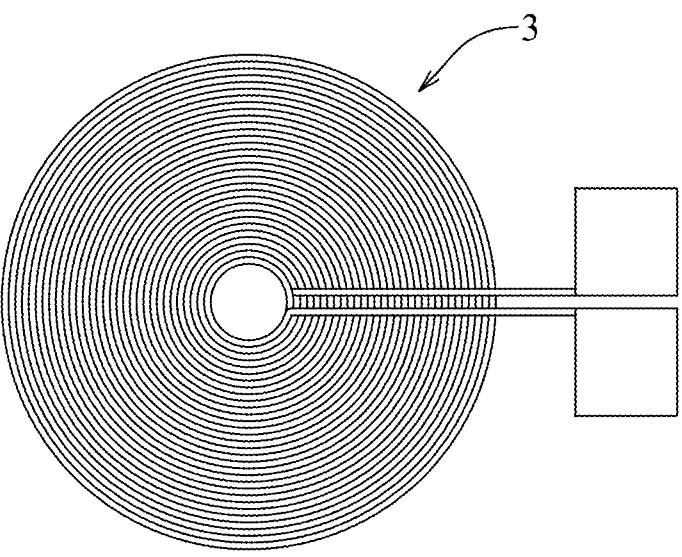
FIG. 8 is a schematic diagram illustrating a third exemplary layout of the capacitive electrode assembly.
Figure 9:
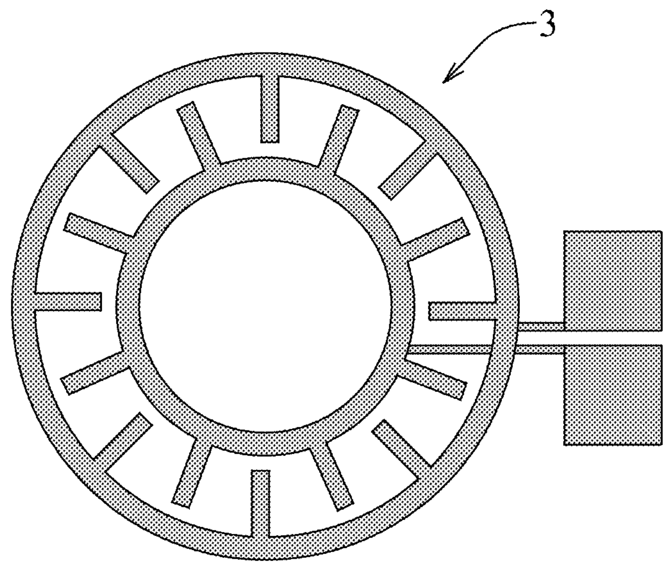
FIG. 9 is a schematic diagram illustrating a fourth exemplary layout of the capacitive electrode assembly.

Further referring to FIG. 3, the capacitive electrode assembly 3 is mounted to the nozzle 12, and is disposed to receive a respiratory airflow from a user who is using the medication atomizer 1 of the automatic dosage-controlled atomizer. The capacitive electrode assembly 3 is configured to have a varying capacitance which is positively correlated to a flow rate of the respiratory airflow. In the illustrative embodiment, as shown in FIGS. 4 and 5, the capacitive electrode assembly 3 includes an outer annular electrode 31 that defines a first hollow area 33, and an inner annular electrode 32 that is disposed in the first hollow area 33 and that defines a second hollow area 34. The inner annular electrode 32 is concentric with the outer annular electrode 31, and the second hollow area 34 has a diameter greater than a diameter of an aerosol outlet 120 of the nozzle 12 (see FIG. 3), so that the aerosol outlet 120 would not be obstructed by the capacitive electrode assembly 3. The varying capacitance may be derived from $C_{sensor}(E)=\varepsilon\times(A/d)$, where $C_{sensor}$ represents the varying capacitance, ε represents permittivity of a medium between the electrodes 31, 32, which may vary with the respiratory airflow during inhalation and exhalation of the user, A represents an area of the electrodes 31, 32, which is a constant, and d represents a distance between the electrodes 31, 32, which is a constant. Therefore, when the permittivity ε changes with the inhalation and the exhalation of the user, the varying capacitance changes accordingly. In some embodiments, the capacitive electrode assembly 3 may be made to include a pair of helical interdigital electrodes that are arranged side by side, extend from contact pads, and wound around from outside toward inside, as shown in FIG. 7. In some embodiments, the capacitive electrode assembly 3 may be made to include a pair of concentric interdigital electrodes that are arranged side by side, extend from contact pads, and wound around from the inside toward the outside, as shown in FIG. 8. In some embodiments, the capacitive electrode assembly 3 may be made to include an outer comb-like annular electrode and an inner comb-like annular electrode that are concentric and interdigitated with each other, as shown in FIG. 9.

Figure 6:
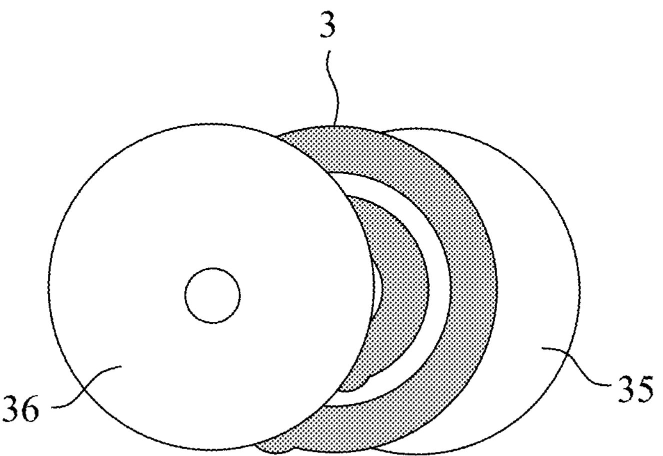
FIG. 6 is a schematic diagram illustrating a shielding plate and a protective plate of the capacitive electrode assembly.

Referring to FIG. 6, the respiration sensor 2 further includes a shielding plate 35 that is disposed distal to the user relative to the capacitive electrode assembly 3, and a protective plate 36 that is disposed close to the user relative to the capacitive electrode assembly 3. In the illustrative embodiment, the shielding plate 35 and the protective plate 36 are disposed at opposite sides of the capacitive electrode assembly 3. The shielding plate 35 is configured for blocking electric fields emitted away from the user by the capacitive electrode assembly 3, so the emission of the electric fields are primarily directed toward an oral cavity of the user. In this embodiment, the protective plate 36 may be a plastic plate for minimizing influence of moisture in the respiratory airflow on the capacitive electrode assembly 3. In this embodiment, the shielding plate 35 may contain metal components for shielding electric fields.

Referring to FIG. 2 again, the resonant circuit 4 is connected to the capacitive electrode assembly 3 in parallel, and includes a capacitor 41, a resistor 42 and an inductor 43.

Figure 10:
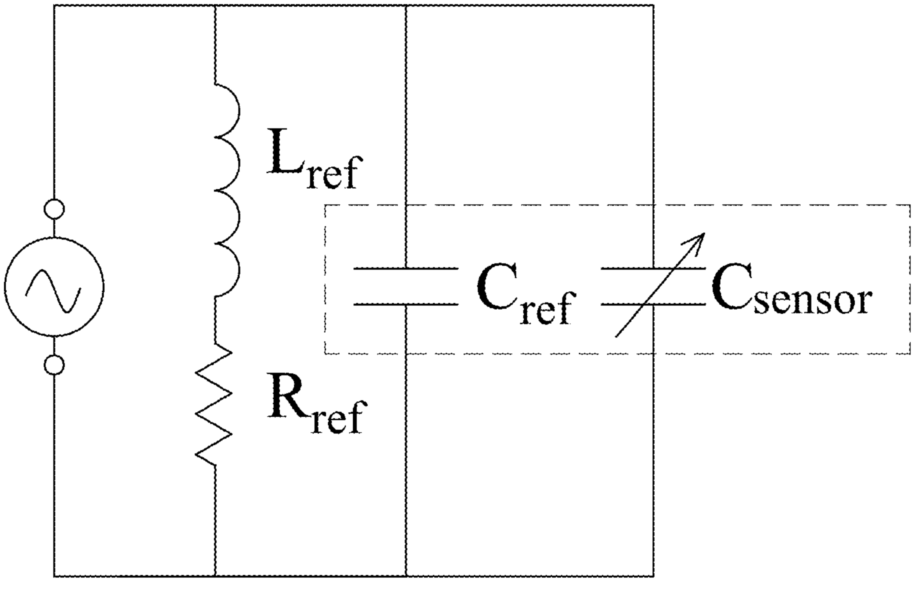
FIG. 10 is a schematic circuit diagram illustrating an equivalent circuit of a combined circuit of the capacitive electrode assembly and a resonant circuit of the embodiment.

The capacitor 41 is connected to the capacitive electrode assembly 3 in parallel. The resistor 42 and the inductor 43 are in series connection, and the series connection of the resistor 42 and the inductor 43 is connected to the capacitive electrode assembly 3 in parallel. Accordingly, the resonant circuit 4 has a reference capacitance from the capacitor 41 and a reference inductance from the inductor 43. Further referring to FIG. 10, an equivalent circuit of a combined circuit of the capacitive electrode assembly 3 and the resonant circuit 4 is illustrated. The combined circuit receives an alternating voltage from the signal analyzing circuit 5 (see FIG. 2), and has the reference inductance ($L_{ref}$) from the inductor 43, a reference resistance ($R_{ref}$) from the resistor 42, and a total capacitance equaling a sum of the reference capacitance ($C_{ref}$) and the varying capacitance ($C_{sensor}$).

The signal analyzing circuit 5 is electrically connected to the resonant circuit 4, is configured to generate and send a feed signal into the resonant circuit 4 in such a way that the resonant circuit 4 generates a resonant signal based on the feed signal, and is configured to perform frequency analysis on the resonant signal to generate a frequency variation signal indicating a frequency variation of the resonant signal. The frequency of the resonant signal can be approximated according to:

$$f_r(\varepsilon) \approx \frac{1}{2\pi\sqrt{L_{ref}(C_{ref} + C_{sensor}(\varepsilon))}},$$

where $f_r$ represents the frequency of the resonant signal. From this equation, it can be seen that the frequency variation of the resonant signal (i.e., variation of $f_r$) would be related to the change of the varying capacitance $C_{sensor}$.

The signal analyzing circuit 5 includes a waveform generator 51, a channel driver 52, a frequency counter 53 and a microcontroller unit (MCU) 54.

Figure 12:
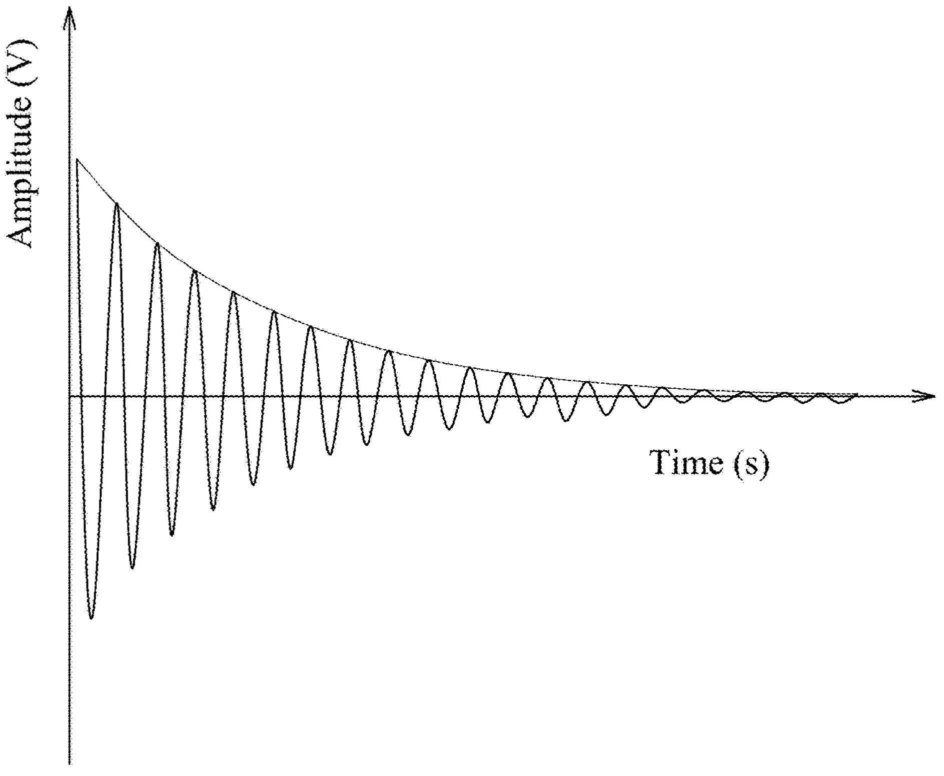
FIG. 12 is a plot illustrating a waveform of a resonant signal generated by the resonant circuit.

In this embodiment, the waveform generator 51 is a square wave generator that is configured to generate a square wave current signal serving as the feed signal, and the channel driver 52 is realized using an application specific integrated circuit (ASIC) labeled as FDC2214. The channel driver 52 is electrically connected to the waveform generator 51 and the resonant circuit 4, and is used to transmit the square wave current signal from the waveform generator 51 to the resonant circuit 4, so as to induce the resonant signal in the resonant circuit 4, and to receive the resonant signal from the resonant circuit 4. Referring to FIG. 12, the resonant signal may be a transient response related to the reference inductance, the reference capacitance and the varying capacitance.

Figure 13:
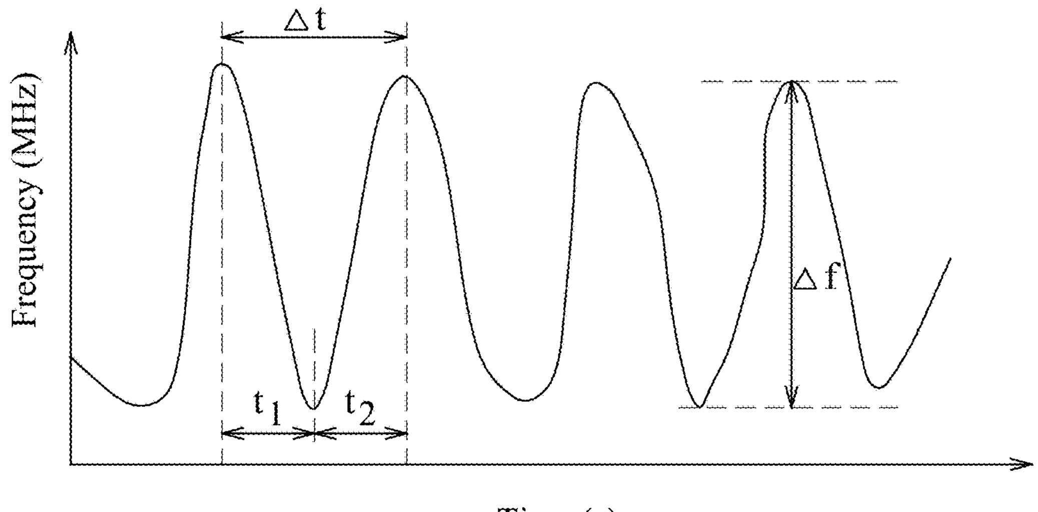
FIG. 13 is a plot illustrating a waveform of a frequency variation signal generated by the respiration sensor.

The frequency counter 53 is electrically connected to the channel driver 52 for receiving the resonant signal therefrom, and is electrically connected to a clock generator (e.g., an oscillator) 55 for receiving a reference frequency signal (e.g., a clock signal) that has a reference frequency. The frequency counter 53 is configured to perform frequency counting on the resonant signal based on the reference frequency signal to generate the frequency variation signal. Referring to FIG. 13, Δf represent the frequency variation of the resonant signal, Δt represents a period time value of a breathing cycle of the user, which is composed of an exhalation time value $t_1$ and an inhalation time value $t_2$.

The MCU 54 is electrically connected to the frequency counter 53 for receiving the frequency variation signal therefrom, and is configured to obtain a detected vital capacity value and a period time data piece based on the frequency variation signal.

The MCU 54 includes a database that records a plurality of vital capacity values, and a plurality of reference frequency variation values that respectively correspond to the vital capacity values. The MCU 54 determines, based on the database, one of the vital capacity values that corresponds to the frequency variation of the resonant signal to be the detected vital capacity value, by comparing the frequency variation of the resonant signal with the reference frequency variation values. Furthermore, the MCU 54 performs periodic analysis on the frequency variation signal to obtain the period time data piece related to the frequency variation signal, where the period time data piece includes the period time value, the exhalation time value and the inhalation time value.

The atomization adjustment module 6 is electrically connected to the signal analyzing circuit 5 for receiving the detected vital capacity value and the period time data piece therefrom, is electrically connected to the medication atomizer 1, and is configured to generate a cumulative effective inhaled dose value based on the detected vital capacity value and the period time data piece. In practice, the atomization adjustment module 6 may be realized as a hardware chip (e.g., an application specific integrated circuit, ASIC), or a software module that is executed by the MCU 54, but this disclosure is not limited in this respect. The cumulative effective inhaled dose value may be calculated according to:

$$EID = TOD \times \frac{t_2}{t_1 + t_2} \times V(\Delta f) \times BPM$$

$$TOD = DR \times t_{total},$$

where EID represents the cumulative effective inhaled dose value, TOD represents a cumulative total output dose of the medication atomizer 1, DR represents a delivery rate of the aerosol airflow (namely, an amount of the aerosol airflow outputted per unit time), $t_{total}$ represents a length of time cumulated since a beginning of delivering the aerosol airflow (i.e., a cumulative delivery time of the aerosol airflow), $t_1$ represents the exhalation time value, $t_2$ represents the inhalation time value, V represents the detected vital capacity value that is related to the frequency variation Δf of the resonant signal, and BPM represents a breathing rate of the user. In this embodiment, the breathing rate BPM is measured in number of breaths per minute, and each of the exhalation time value $t_1$ and the inhalation time value $t_2$ is measured in seconds, so $BPM=60/(t_1+t_2)$. In practice, the detected vital capacity value and the breathing rate may be used as a reference for adjusting the spray output module 11 in terms of the delivery rate and a length of time for delivering the aerosol airflow, thereby attaining precise control of a dosage amount. In some embodiments, the delivery rate may be fixed. In some embodiments, the delivery rate may be dynamically adjusted by the atomization adjustment module 6 based on the detected vital capacity value and the breathing rate, so as to achieve cost savings on medication and avoid medication wastage.

The atomization adjustment module 6 is configured to compare the cumulative effective inhaled dose value with a predetermined dose threshold value to generate and send a control signal to the medication atomizer 1. When the cumulative effective inhaled dose value exceeds the predetermined dose threshold value, the control signal is made to cause the medication atomizer 1 to stop generation of the aerosol airflow. When the cumulative effective inhaled dose value does not exceed the predetermined dose threshold value, the control signal is made to cause the medication atomizer 1 to continue generation of the aerosol airflow. In other words, the atomization adjustment module 6 is configured to perform real-time monitoring on whether an end point of inhaling medication has been reached. If the end point of inhaling medication has been reached, the atomization adjustment module 6 immediately and automatically controls the medication atomizer 1 to stop atomization so the user will not inhale excessive dosage of medication, thereby providing optimal treatment for the user and achieving precision medicine application.

Figure 11:
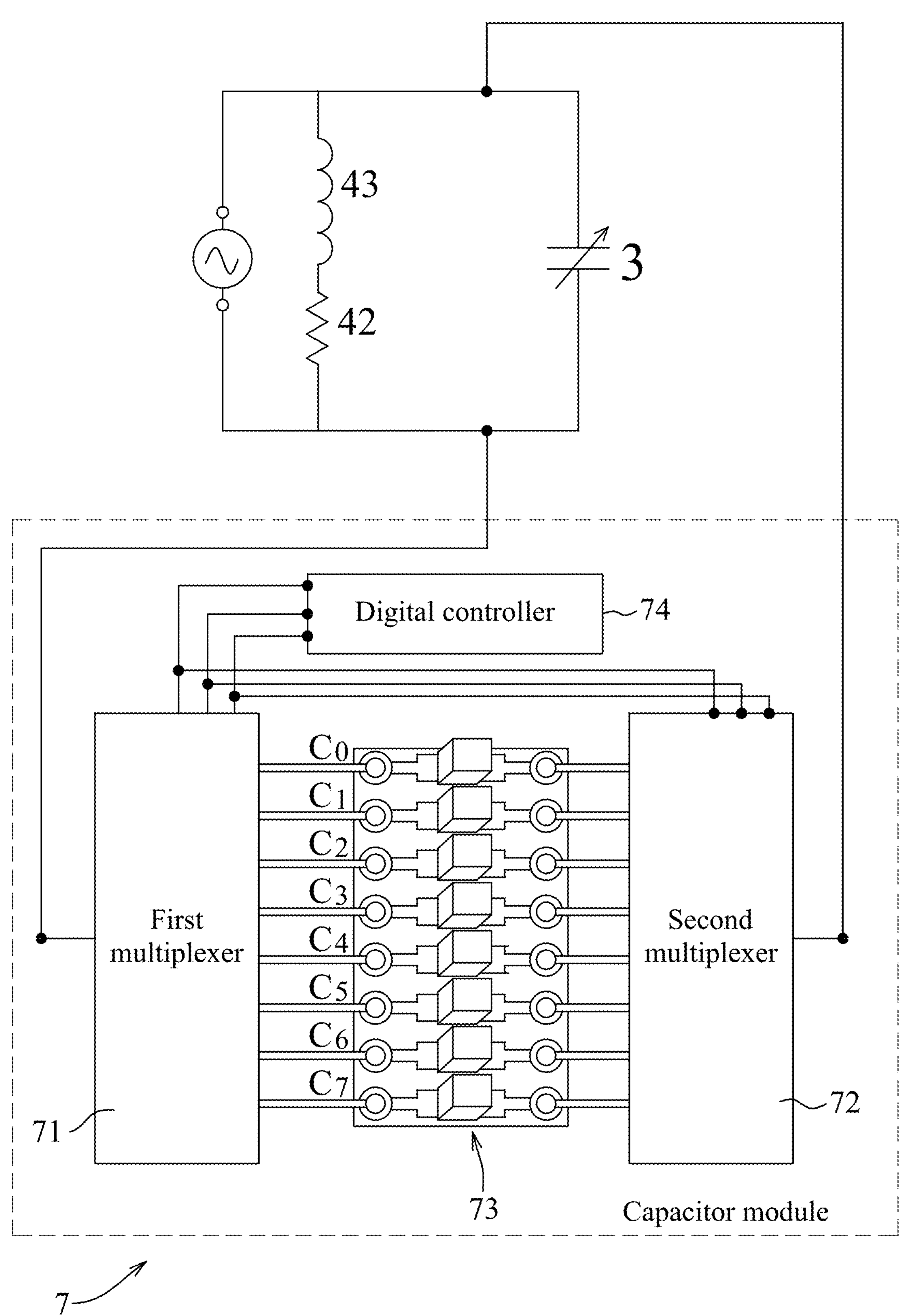
FIG. 11 is a block diagram illustrating a variation of the resonant circuit.

Referring to FIG. 11, in one embodiment, the capacitor 41 (see FIG. 2) may be replaced by a capacitor module 7 to provide the reference capacitance. The capacitor module 7 includes a first multiplexer 71, a second multiplexer 72, a capacitor array 73 that is connected between the first multiplexer 71 and the second multiplexer 72, and a digital controller 74 that is electrically connected to control terminals of the first multiplexer 71 and the second multiplexer 72. In the illustrative embodiment, the capacitor array 73 is exemplified to include eight capacitors $C_0$ to $C_7$, but this disclosure is not limited in this respect. The first multiplexer 71 has an input terminal electrically connected to the resistor 42, and multiple output terminals each being connected to one end of a respective one of the capacitors $C_0$ to $C_7$ of the capacitor array 73. The second multiplexer 72 has an input terminal electrically connected to the inductor 43, and multiple output terminals each being connected to another end of a respective one of the capacitors $C_0$ to $C_7$ of the capacitor array 73. Each of the first multiplexer 71 and the second multiplexer 72 is operable by the digital controller 74 to establish electrical connection between the input terminal thereof and one of the output terminals thereof, while the input terminal is disconnected from other output terminals. The digital controller 74 may be realized using a microprocessor, such as ATmega328 from Atmel®, but this disclosure is not limited in this respect. Before using the automatic dosage-controlled atomizer, the user may perform inhalation and exhalation with the respiratory sensor 2 while operating the digital controller 74 to connect the capacitive electrode assembly 3 to the capacitors $C_0$ to $C_7$ in turns and induce multiple resonant signals that respectively correspond to the capacitors $C_0$ to $C_7$. The MCU 54 performs signal-to-noise ratio (SNR) analysis on the resonant signals (e.g., using the frequency variation signals derived from the resonant signals), and the user may connect the respiration sensor 2 to a computer for displaying a result of the SNR analysis, and then select one of the capacitors $C_0$ to $C_7$ of which the corresponding resonant signal has the greatest SNR to provide the reference capacitance in subsequent usage of the automatic dosage-controlled atomizer.

In summary, the embodiments of this disclosure uses real-time respiratory information (e.g., the breathing rate and the detected vital capacity value) and the delivery rate and the cumulative delivery time of the aerosol airflow to perform real-time monitoring on whether the end point of inhaling medication has been reached, thereby achieving optimal treatment. Furthermore, the above function can be achieved by simply attaching the respiration sensor 2 to the medication atomizer 1, with no structural change applied to the medication atomizer 1. Since the respiratory monitoring is performed using the contactless capacitive coupling technique, and the protective plate 36 is used to minimize influence of moisture and sanitary issues on the capacitive electrode assembly 3, the life of the respiration sensor 2 may be prolonged.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects; such does not mean that every one of these features needs to be practiced with the presence of all the other features. In other words, in any described embodiment, when implementation of one or more features or specific details does not affect implementation of another one or more features or specific details, said one or more features may be singled out and practiced alone without said another one or more features or specific details. It should be further noted that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. An automatic dosage-controlled atomizer, comprising:

a medication atomizer that is configured to generate an aerosol airflow, and that includes a nozzle for delivering the aerosol airflow; and a respiration sensor that includes:

a capacitive electrode assembly that is mounted to said nozzle, that is disposed to receive a respiratory airflow from a user who is using said automatic dosage-controlled atomizer, and that is configured to have a varying capacitance which is positively correlated to a flow rate of the respiratory airflow;

a resonant circuit that is configured to have a reference inductance and a reference capacitance, and that is connected to said capacitive electrode assembly in parallel, so as to induce a total capacitance equaling a sum of the varying capacitance and the reference capacitance for a combined circuit of said capacitive electrode assembly and said resonant circuit;

a signal analyzing circuit that is electrically connected to said resonant circuit, and that is configured to generate and send a feed signal to said resonant circuit in such a way that said resonant circuit generates a resonant signal based on the feed signal, and to perform frequency analysis on the resonant signal to generate a frequency variation signal indicating a frequency variation of the resonant signal, where the frequency variation of the resonant signal is related to the varying capacitance; and an atomization adjustment module that is electrically connected to said signal analyzing circuit and said medication atomizer;

wherein said signal analyzing circuit includes a database that records a plurality of vital capacity values, and a plurality of reference frequency variation values that respectively correspond to the vital capacity values;

wherein said signal analyzing circuit is configured to, based on said database, determine one of the vital capacity values that corresponds to the frequency variation of the resonant signal to be a detected vital capacity value by comparing the frequency variation of the resonant signal with the reference frequency variation values;

wherein said signal analyzing circuit is configured to perform periodic analysis on the frequency variation signal to obtain a period time data piece related to the frequency variation signal, where the period time data piece includes an inhalation time value and an exhalation time value;

wherein said atomization adjustment module is configured to receive the detected vital capacity value and the period time data piece from said signal analyzing circuit, and to generate a cumulative effective inhaled dose value based on the detected vital capacity value and the period time data piece; and wherein said atomization adjustment module is configured to compare the cumulative effective inhaled dose value with a predetermined dose threshold value to generate and send a control signal to said medication atomizer in such a way that said medication atomizer stops generation of the aerosol airflow when the cumulative effective inhaled dose value exceeds the predetermined dose threshold value.

2. The automatic dosage-controlled atomizer as claimed in claim 1, wherein said capacitive electrode assembly includes an outer annular electrode that defines a first hollow area, and an inner annular electrode that is disposed in said first hollow area and that defines a second hollow area;

wherein said inner annular electrode is concentric with said outer annular electrode, and said second hollow area has a diameter greater than a diameter of an aerosol outlet of said nozzle.

3. The automatic dosage-controlled atomizer as claimed in claim 1, wherein said respiration sensor further includes:

a shielding plate that is disposed distal to the user relative to said capacitive electrode assembly, and that is configured for blocking electric fields emitted away from the user by said capacitive electrode assembly; and a protective plate that is disposed close to the user relative to said capacitive electrode assembly.

4. The automatic dosage-controlled atomizer as claimed in claim 1, wherein said resonant circuit includes a capacitor connected to said capacitive electrode assembly in parallel, and a resistor and an inductor that are arranged in a series connection;

wherein the series connection of said resistor and said inductor are connected to said capacitive electrode assembly in parallel.

5. The automatic dosage-controlled atomizer as claimed in claim 1, wherein said signal analyzing circuit includes:

a waveform generator configured to generate the feed signal;

a channel driver electrically connected to said waveform generator and said resonant circuit, and configured to transmit the feed signal from said waveform generator to said resonant circuit to induce the resonant signal in said resonant circuit, and to receive the resonant signal from said resonant circuit;

a frequency counter electrically connected to said channel driver for receiving the resonant signal therefrom, and configured to perform frequency counting on the resonant signal based on a reference frequency signal to generate the frequency variation signal; and a microcontroller unit electrically connected to said frequency counter for receiving the frequency variation signal therefrom, and configured to obtain the detected vital capacity value and the period time data piece based on the frequency variation signal.

6. The automatic dosage-controlled atomizer as claimed in claim 1, wherein the cumulative effective inhaled dose value is generated according to:

$$EID = TOD \times \frac{t_2}{t_1 + t_2} \times V(\Delta f) \times BPM,$$

where EID represents the cumulative effective inhaled dose value, TOD represents a cumulative total output dose of said medication atomizer, $t_1$ represents the exhalation time value, $t_2$ represents the inhalation time value, V(Δf) represents the detected vital capacity value that is related to the frequency variation of the resonant signal, and BPM represents a breathing rate of the user.

7. The automatic dosage-controlled atomizer as claimed in claim 6, wherein $TOD=DR \times t_{total}$, where DR represents a delivery rate of the aerosol airflow, and $t_{total}$ represents a length of time cumulated since a beginning of delivering the aerosol airflow.

8. The automatic dosage-controlled atomizer as claimed in claim 6, wherein BPM is measured in number of breaths per minute, each of $t_1$ and $t_2$ is measured in seconds, and $BPM=60/(t_1+t_2)$.

9. A respiration sensor for use with a medication atomizer, the medication atomizer being configured to generate an aerosol airflow, and including a nozzle for delivering the aerosol airflow, said respiration sensor comprising:

a capacitive electrode assembly that is to be mounted to the nozzle, that is disposed to receive a respiratory airflow from a user, and that is configured to have a varying capacitance which is positively correlated to a flow rate of the respiratory airflow;

a resonant circuit that is configured to have a reference inductance and a reference capacitance, and that is connected to said capacitive electrode assembly in parallel;

a signal analyzing circuit that is electrically connected to said resonant circuit, and that is configured to generate and send a feed signal to said resonant circuit in such a way that said resonant circuit generates a resonant signal based on the feed signal, and to perform frequency analysis on the resonant signal to generate a frequency variation signal indicating a frequency variation of the resonant signal, where the frequency variation of the resonant signal is related to the varying capacitance; and an atomization adjustment module that is electrically connected to said signal analyzing circuit and that is to be connected to the medication atomizer;

wherein said signal analyzing circuit includes a database that records a plurality of vital capacity values, and a plurality of reference frequency variation values that respectively correspond to the vital capacity values;

wherein said signal analyzing circuit is configured to, based on said database, determine a detected vital capacity value that is one of the vital capacity values and that corresponds to the frequency variation of the resonant signal by comparing the frequency variation of the resonant signal with the reference frequency variation values;

wherein said signal analyzing circuit is configured to perform periodic analysis on the frequency variation signal to obtain a period time data piece related to the frequency variation signal, where the period time data piece includes an inhalation time value and an exhalation time value;

wherein said atomization adjustment module is configured to receive the detected vital capacity value and the period time data piece from said signal analyzing circuit, and to generate a cumulative effective inhaled dose value based on the detected vital capacity value and the period time data piece; and wherein said atomization adjustment module is configured to compare the cumulative effective inhaled dose value with a predetermined dose threshold value to generate and send a control signal to said medication atomizer in such a way that said medication atomizer stops generation of the aerosol airflow when the cumulative effective inhaled dose value exceeds the predetermined dose threshold value.

10. The respiration sensor as claimed in claim 9, wherein said signal analyzing circuit includes:

a waveform generator configured to generate the feed signal;

a channel driver electrically connected to said waveform generator and said resonant circuit, and configured to transmit the feed signal from said waveform generator to said resonant circuit to induce the resonant signal in said resonant circuit, and to receive the resonant signal from said resonant circuit;

a frequency counter electrically connected to said channel driver for receiving the resonant signal therefrom, and configured to perform frequency counting on the resonant signal based on a reference frequency signal to generate the frequency variation signal; and a microcontroller unit electrically connected to said frequency counter for receiving the frequency variation signal therefrom, and configured to obtain the detected vital capacity value and the period time data piece based on the frequency variation signal.

* * * * *